(12) United States Patent
Tsai et al.

(10) Patent No.: US 8,111,390 B2
(45) Date of Patent: Feb. 7, 2012

(54) METHOD AND APPARATUS FOR RESIDUE DETECTION IN THE EDGE DELETED AREA OF A SUBSTRATE

(75) Inventors: Kenneth Tsai, Emerald Hills, CA (US); Asaf Schlezinger, Sunnyvale, CA (US)

(73) Assignee: Applied Materials, Inc., Santa Clara, CA (US)

( * ) Notice: Subject to any disclaimer, the term of this patent is extended or adjusted under 35 U.S.C. 154(b) by 342 days.

(21) Appl. No.: 12/425,806

(22) Filed: Apr. 17, 2009

(65) Prior Publication Data

US 2010/0265497 A1    Oct. 21, 2010

(51) Int. Cl.
*G01N 21/00* (2006.01)

(52) U.S. Cl. ............ 356/239.1; 356/237.2; 356/630; 250/559.36

(58) Field of Classification Search .... 356/237.1–237.5, 356/239.1, 239.7–239.8, 394, 630–632; 250/559.27, 250/559.28, 559.36, 559.4
See application file for complete search history.

(56) References Cited

U.S. PATENT DOCUMENTS

| | | | |
|---|---|---|---|
| 5,461,007 A | | 10/1995 | Kobayashi |
| 5,626,675 A | * | 5/1997 | Sakamoto et al. ............ 118/663 |
| 7,070,479 B2 | | 7/2006 | Faustmann et al. |
| 7,280,197 B1 | * | 10/2007 | Rosengaus ................. 356/237.1 |
| 2003/0139048 A1 | * | 7/2003 | Wong et al. .................... 438/692 |
| 2004/0138838 A1 | * | 7/2004 | Scheiner et al. ................ 702/64 |
| 2005/0023491 A1 | * | 2/2005 | Young et al. ............. 250/559.42 |
| 2006/0138368 A1 | | 6/2006 | Lee |
| 2007/0196566 A1 | * | 8/2007 | Takeishi et al. ............... 427/145 |

FOREIGN PATENT DOCUMENTS

| | | |
|---|---|---|
| JP | 05-062952 | 8/1991 |
| JP | 2007-299910 | 11/2007 |
| KR | 2006-0077021 | 7/2006 |

OTHER PUBLICATIONS

PCT International Search Report and Written Opinion in PCT/US2010/031364, dated Nov. 18, 2010, 9 pgs.

* cited by examiner

*Primary Examiner* — Hoa Pham

(74) *Attorney, Agent, or Firm* — Diehl Servilla LLC

(57) ABSTRACT

Apparatus and methods for detecting residue on a glass substrate and method of use are disclosed. The apparatus comprises a substrate support, a sensor, a controller and a peripheral device in communication with the controller. The apparatus measures the height or thickness of a main surface and an edge delete surface of a substrate to determine if film residue is present on the edge delete surface.

20 Claims, 5 Drawing Sheets

METHOD AND APPARATUS FOR RESIDUE DETECTION IN THE EDGE DELETED AREA OF A SUBSTRATE

BACKGROUND OF THE INVENTION

1. Field of the Invention

Embodiments of the present invention generally relate to manufacturing thin film photovoltaic devices, and more particularly, to detecting residue depth in the edge deletion zone of a photovoltaic device resulting from insufficient removal of the thin film.

2. Description of the Related Art

In thin film photovoltaic manufacturing, it is necessary to remove the film deposition at the edges of the glass panel after all films have been deposited. This is commonly referred to as edge deletion. Edge deletion is performed, primarily to electrically isolate the photovoltaic module from metal frames and to aid in sealing the module from moisture.

Edge deletion methods vary greatly from sand-blasting to grinding and laser ablation, amongst other techniques. Regardless of the deletion method employed, it is important to ensure that there is no thin film residue in the edge delete zone. Thus, there is a need in the art for systems and methods for detecting deposition residue in the edge deleted area.

SUMMARY OF THE INVENTION

One or more embodiment of the invention are directed to apparatus for detecting residue on a portion of a glass substrate surface. The apparatus comprises a platform for supporting the substrate having a ground edge portion. A laser sensor having at least one sensor head is arranged such that the sensor and the substrate can be moved with respect to each other so that the sensor traverses the substrate surface, including a main surface and the ground edge portion of the substrate surface. The apparatus includes a controller in communication with the sensor head to receive data from the sensor head, the controller operable to interpret data obtained from the sensor head to determine if residue is present on the edge surface.

One or more embodiments of the invention are directed to methods of detecting residue on a glass substrate including a main surface having a height and a coating thereon and an edge surface having a height that is not greater than the height of the main surface. A laser sensor is positioned a distance from the main surface and an average main surface distance from a laser sensor is obtained from a plurality of measurements across the main surface. A minimum edge distance or average edge distance from the laser sensor is measured. Whether residue is present on the edge surface is determined by comparing the minimum edge distance or average edge distance from the laser sensor to the average main surface distance from the laser sensor.

One or more embodiments of the invention are directed to methods of detecting residue on a glass substrate including a main surface having a coating thereon defining a main surface thickness and an edge surface having a thickness that is not greater than the thickness of the main surface. An average thickness of the main surface is determined from a plurality of measurements obtained with a laser sensor spaced from the main surface. A maximum thickness or average thickness of the edge surface is determined from a plurality of measurements using the laser sensor. Whether residue is present on the edge surface is determined by comparing the maximum edge thickness or average edge thickness to the average main surface thickness.

The foregoing has outlined rather broadly certain features and technical advantages of the present invention. It should be appreciated by those skilled in the art that the specific embodiments disclosed may be readily utilized as a basis for modifying or designing other structures or processes within the scope present invention. It should also be realized by those skilled in the art that such equivalent constructions do not depart from the spirit and scope of the invention as set forth in the appended claims.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Embodiments of the present invention provide methods and apparatus for detecting residue in the edge delete zone of a photovoltaic module. Indirect measurements may be used to determine the non-uniform profile of the ground edge, utilizing minimum and average ground heights to infer the presence of residue in the edge delete zone. When the ground height is less than a target value, insufficient material has been removed and residue is likely present. When the ground height meets the target value, sufficient glass has been removed and no deposition residue should be present.

Figure 1A:
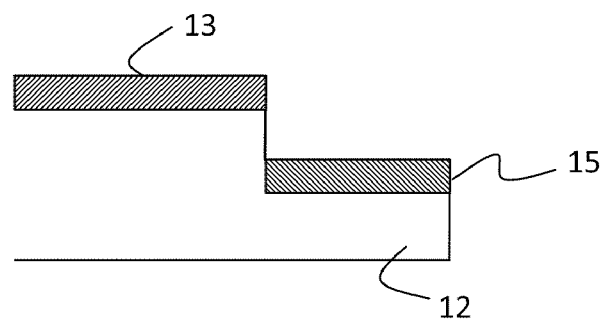
FIGS. 1A-1E illustrate several profile which may result from the removal of a thin film along the edge delete zone.
Figure 1B:
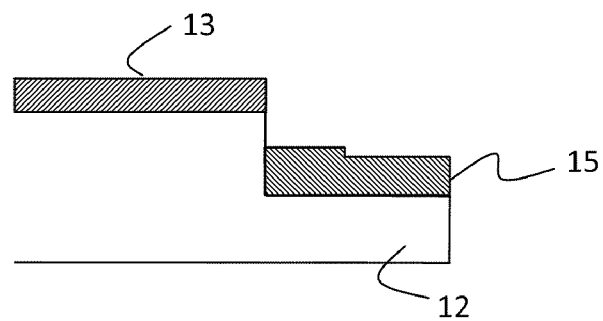
Figure 1C:
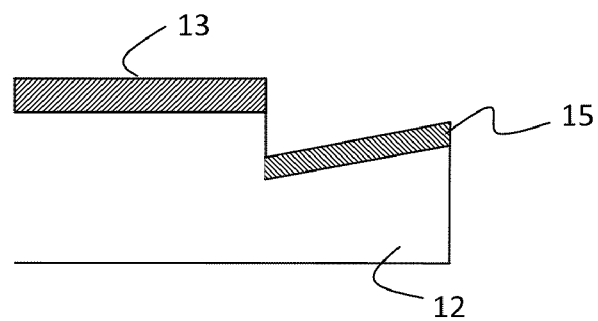
Figure 1D:
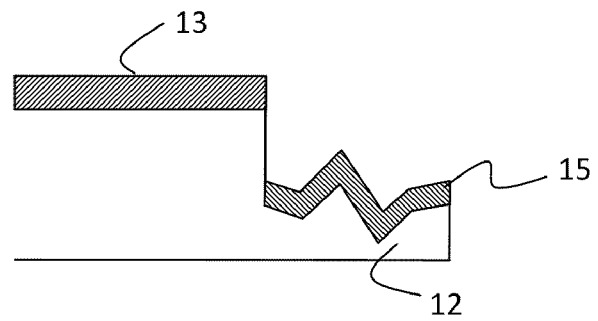

After grinding the edge of the photovoltaic module, the ground surface is likely to not be flat and can have various profiles. Some examples of these profiles can be seen in FIGS. 1A-1E. FIG. 1A shows a substrate 12 having a thin film coating 13 and a flat ground glass edge delete zone 15. This would be an ideal cross-sectional profile, but an ideal profile is unlikely to occur due to imperfections and irregularities in the grinding technique or deletion method. FIG. 1B shows the substrate 12 with a stepped edge delete zone 15, stepping down towards the outer edge of the substrate. The pattern shown is for illustration only; there can also be multiple steps of various heights. FIG. 1C shows a substrate 12 with an inward sloping ground glass edge delete zone 15. The slope is shown with the height increasing toward the edge of the substrate 12, but the slope can be in either direction or have multiple portions with different slopes, as shown in FIG. 1D.

The various edge profiles shown in FIGS. 1A-1D exhibit no residue from the thin film coating 13. So, while not necessarily ideal, each profile provides sufficient electrical isolation of the photovoltaic module.

Figure 1E:
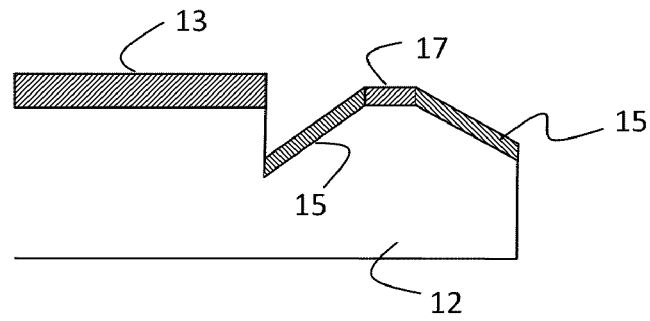

FIG. 1E, however, shows a substrate 12 with a thin film 13 and an edge delete zone with residue. The profile exhibits residue free ground glass portions 15 and a residue coated portion 17 which is undesirable in a completed photovoltaic module. The edge deleted zone 15, which may also be referred to as the edge deleted area, is typically less than 20 mm wide. In some aspects of the invention the edge deleted zone 15 is between about 10 mm and about 14 mm wide. In further detailed aspects, the edge deleted zone 15 is less than about 20 mm, 19 mm, 18 mm, 17 mm, 16 mm, 15 mm or 14 mm wide. In additional detailed aspects, the edge deleted zone 15 is greater than about 5 mm, 6 mm, 7 mm, 8 mm, 9 mm or 10 mm wide. Combinations of the minimum and maximum zone widths can be seen in further aspects of the invention.

Figure 2:
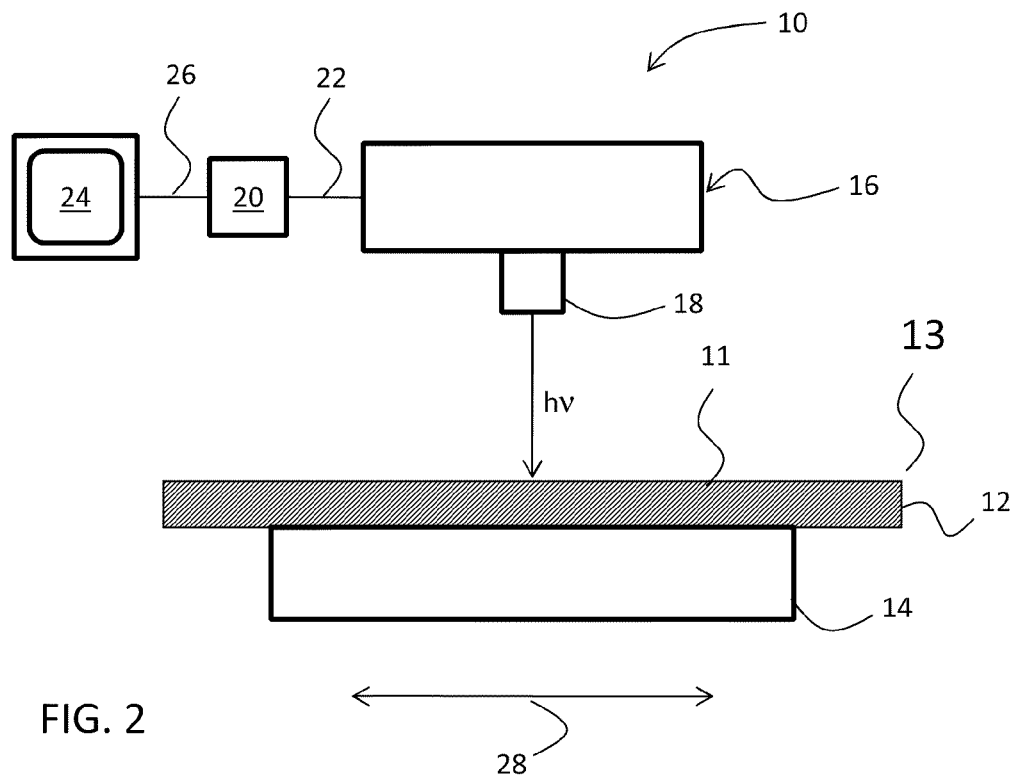
FIG. 2 illustrates a residue detection system according to one or more embodiments of the invention.
Figure 3:
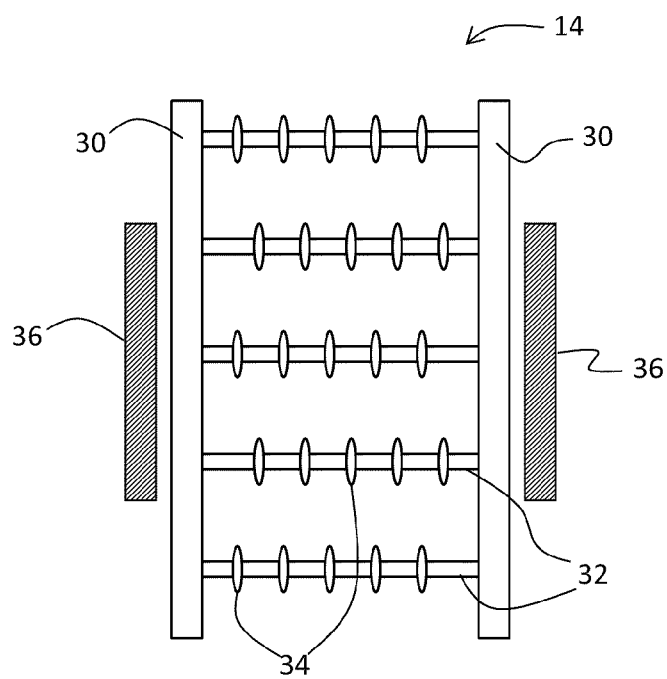
FIG. 3 illustrates a table for a residue detection system according to one or more embodiments of the invention.

An embodiment of an apparatus 10 for detecting residue on a glass substrate 12 is shown in FIGS. 2 and 3. The apparatus 10 includes a platform 14 for supporting a substrate 12 having a surface 11 including a ground edge portion 13 (as shown in FIGS. 1A-1E) and a sensor, which in specific embodiments, is a laser sensor 16. The platform 14 can be horizontal, vertical or angled, depending on user preference, space requirements, etc. In the embodiment shown, the laser sensor 16 has at least one sensor head 18. The sensor head 18 and the substrate 12 are moveable with respect to each other so that the sensor head 18 can traverse the surface 11 of the substrate, including the ground edge portion 13 to scan for residue on the edge portion 13. A controller 20 communicates with the sensor head 18 via connection 22. The controller 20 is capable of interpreting data obtained from the laser sensor 16 through the sensor head 18 and can perform calculations on the data to determine if residue is present on the edge portion of the substrate 12. A peripheral device 24 communicates with the controller 20 via connection 26. The controller 20 is capable of displaying information and controls to a user.

According to certain embodiments, as shown in FIG. 3, a horizontal platform 14 comprises a table having a pair of parallel side members 30. A plurality of cross members 32 are attached to the side members 30. Each of the cross members 32 has a plurality of supports 34 for supporting the substrate 12. The supports 34 can be any suitable support devices, including but not limited to, roller bearings, and rubber rings. The supports 34 allow the substrate 12 to be moved horizontally 28 beneath the laser sensor 16. A locking frame 36 may be used to prevent the table from moving during use. In other embodiments, the platform 14 may hold the substrate 12 in a vertical or inclined orientation. In these embodiments, laser sensor 16 is mounted so as to project light toward the substrate and the substrate 12 is moved within the plane of the platform.

The apparatus 10 of some embodiments includes a substantially flat surface 19 (shown in FIG. 5.) for holding the substrate 12. The substantially flat surface may be positioned on the supports 34 and can support the substrate 12 during measurements and act as a reference point.

Figure 4:
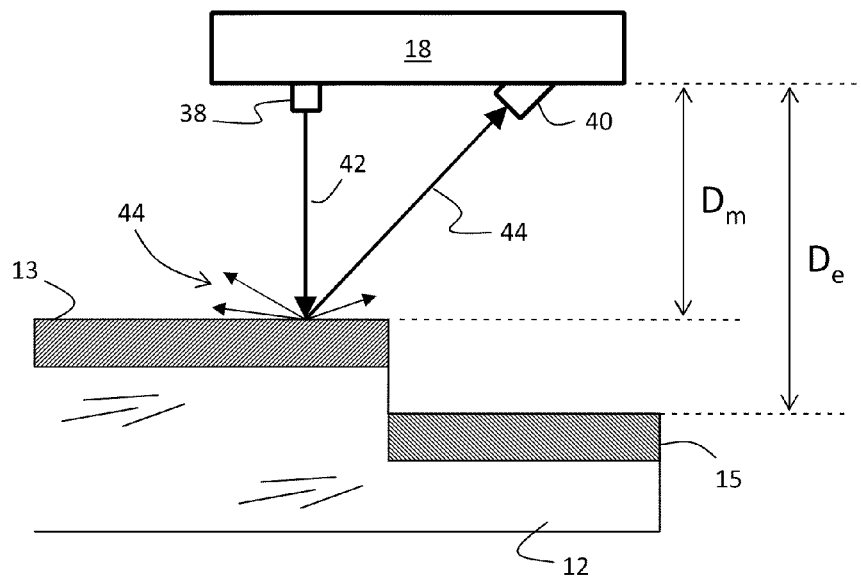
FIG. 4 illustrates operation of a residue detection according to one or more embodiments of the invention.
Figure 5:
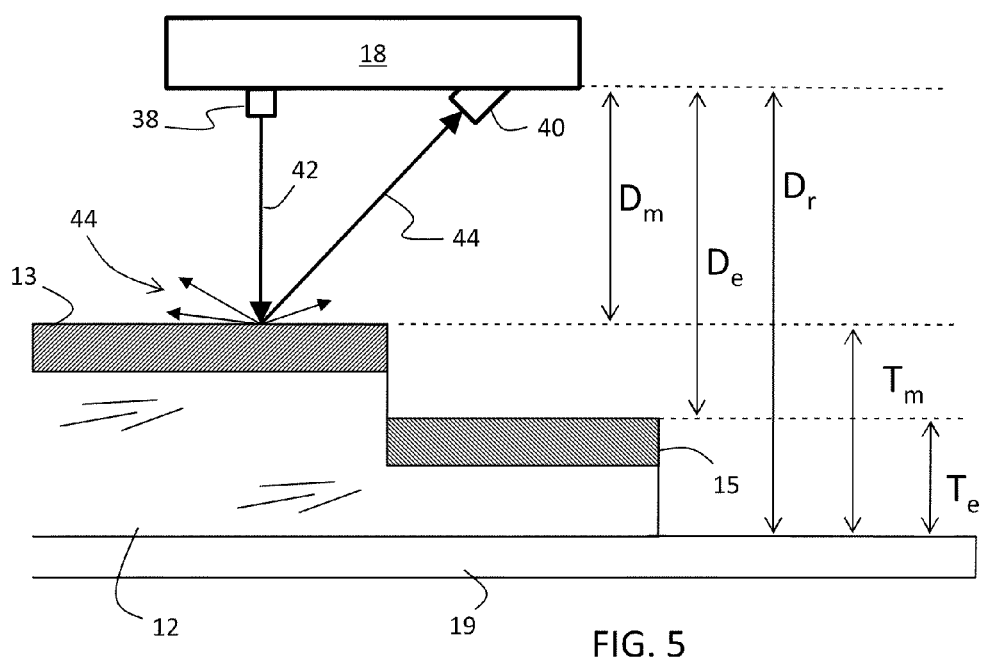
FIG. 5 illustrates operation of a residue detection according to one or more embodiments of the invention.

Referring to FIGS. 4 and 5, the sensor head 18 has a laser source 38 and a detector 40. The laser source 38 and detector 40 are shown protruding from the surface of the sensor head 18, but this configuration is not necessary. For example, these components can be flush mounted in the sensor head 18. The laser source 38 directs a beam of coherent light 42 (laser beam) at the surface of the thin film coating 13 on the substrate 12, the edge delete zone 15 or the flat surface 19. The detector 40 of the laser sensor 16 measures the diffuse reflections 44 which occur from the surface.

The detector 40 is shown displaced from the laser source 38 and positioned on an angle to measure diffuse reflections. This is for illustrative purposes only and should not be taken as limiting the mode of operation of the sensor head 18. In some aspects, the sensor head 18 has a resolution greater than about 1 μm. In other specific aspects, the resolution is greater than about 0.5 μm, 1 μm, 2 μm, 3 μm, 4 μm or 5 μm.

In some aspects, the laser source 38 emits a laser beam 42 having wavelengths within the visible region. In other aspects, the laser source 38 may be configured to emit radiation with wavelengths that fall outside the visible region (e.g., ultraviolet, infrared and microwave). In a specific embodiment, the laser source 38 is configured to emit radiation with a wavelength about 650 nm.

Other embodiments of the invention include a peripheral device 24 capable of graphically displaying information for a user. The peripheral device 24 may be adapted to receive information from the controller 20 and the laser sensor 16 and evaluate the information to determine whether residue exists on the substrate. In some aspects, the peripheral device 24 can offer adjustable controls to the user. The adjustable controls may allow the user to tune the system and specify desired parameters.

When the apparatus described above is placed in operation, methods of detecting residue on a glass substrate 12 are provided. With reference to FIG. 4, the substrate 12 includes a main surface having a height and a thin film coating 13 thereon and an edge surface 15 having a height. The height of the edge surface 15 is not greater than the height of the main surface. A laser sensor 18 is positioned a distance from the main surface. The laser sensor 18 includes a laser source 38 and a detector 40. The laser source 38 directs light 42 toward the surface being measured. The surface can be the substrate 12, the thin film 13, the edge zone 15 of a flat surface 19 that supports the substrate 12. The light 42 is reflected from the surface as diffuse reflections 44 and is measured by detector 40. The distance between the laser sensor 18 and the surface being measured is determined from the diffuse reflections 44.

An average main surface distance ($D_m$) from the laser sensor 18 is measured based on a plurality of surface measurements. The laser sensor 18 is moved relative to the substrate 12 so that it is positioned over the edge deleted region 15. This can be achieved be either movement of the laser sensor 18 or movement of the substrate 12. The edge distance is measured using the laser sensor 18 and a minimum edge distance ($D_e$) is determined. The minimum edge distance $D_e$ can be determined by multiple methods, all of which fall within the scope of the invention. One method is to measure the diffuse reflectivity from a plurality of points in the edge deleted zone and taking the minimum value of all measurements. Another method would be to determine the minimum edge distance $D_e$ at each of a plurality of points. A determination of whether residue is present on the edge surface 15 is made by comparing the minimum edge distance $D_e$ from the laser sensor 18 to the average main surface distance $D_m$. A further method would be to determine the average edge distance $D_e$ at each of a plurality of points. A determination of whether residue is present on the edge surface 15 is made by comparing the average edge distance $D_e$ from the laser sensor 18 to the average main surface distance $D_m$.

According to some aspects of the invention, the average main surface distance from the laser sensor may be obtained by placing the substrate 12 on a flat surface and positioning the laser sensor 18 above the main surface. The main surface can then be scanned with the laser sensor 18 over a plurality of points, thereby measuring a plurality of distances between the laser sensor 18 and the main surface.

In other aspects of the invention the minimum edge distance from the laser sensor 18 is measured by placing the substrate 12 on a flat surface and positioning the laser sensor 18 above the edge surface. The edge surface is then scanned with the laser sensor 18 over a plurality of points, measuring the distance between the laser sensor 18 and the edge surface throughout the scan. The minimum edge distance is determined based on the plurality of distances measured.

One method of analyzing the data is to compare the minimum edge distance at each measurement to the average surface distance adjacent the measured edge. This has the advantage of correcting for any subtle difference in the thickness of the substrate 12. Another method would be to evaluate the absolute minimum edge distance from all edge distance measurements and compare that value to the average main surface distance for the substrate.

In some aspects of the invention a threshold value is established for determining whether residue is present. The threshold value is a measure of the distance by which the main surface distance should differ from the edge surface distance. For example, if the threshold value is set to 20 μm, the edge surface distance would have to be at least about 20 μm greater than the main surface distance to meet the threshold criteria.

Residue would be considered present on the edge surface when the minimum edge distance (or average edge distance, if used) from the laser sensor is about the same as the sum of the average main surface distance from the laser sensor and the threshold value. Residue would not be considered present on the edge surface when the minimum edge distance, or average edge distance, from the laser sensor is greater than the sum of the average main surface distance and the threshold value.

As would be understood by those skilled in the art, the apparatus and methods described herein can be used to measure the step height between the edge delete zone and the main surface. This step height can be measured regardless of the determination of whether residue is present in the edge delete zone.

As illustrated by FIG. 5, further embodiments of the invention are directed to methods of detected residue on a glass substrate 12 based on the thickness of the main surface versus the edge surface. The glass substrate 12 has a main surface with a thin film 13 and an edge surface. The main surface in conjunction with the back surface of the substrate defines a main surface thickness. The edge surface in conjunction with the back surface of the substrate defines an edge surface thickness which is not greater than the main surface thickness. The average thickness of the main surface is determined from a plurality of measurements made with the laser sensor 18. The maximum thickness, or average thickness, of the edge surface is determined from a plurality of measurements made with the laser sensor 18. Whether residue is present on the edge surface is determined by comparing the thickness of the edge surface to the thickness of the main surface.

In some aspects of the invention, the average thickness of the main surface is determined by first measuring the average distance from the laser sensor 18 to the reference surface 19, denoted as $D_r$ on FIG. 5. The substrate 12 is placed on the support surface 19 and the average distance between the laser sensor 18 and the main surface 13 is determined using a plurality of measurements, denoted as $D_m$. The thickness of the substrate main surface, $T_m$, is determined by subtracting the average main surface distance, $D_m$, from the average reference surface distance, $D_r$.

In other aspects of the invention, the average thickness of the edge surface is determined by first measuring an average reference distance between the laser sensor 18 and a flat support surface 19 using a plurality of measurements, denoted $D_r$. A substrate 12 having an edge deleted zone 15 is placed on the support surface 19 and the minimum edge surface distance, or average edge surface distance, between the laser sensor 18 and the edge surface 15 is determined using a plurality of measurements, denoted as $D_e$. The thickness of the edge surface area, $T_e$, of the substrate is determined by subtracting the edge surface distance, $D_e$, from the reference surface distance, $D_r$.

According to some aspects, a threshold value representing a minimum thickness difference is established. To determine whether residue is present on the edge surface, the thickness of the edge surface, $T_e$, is compared to the thickness of the main surface, $T_m$, less the threshold value. Residue would be considered present on the edge surface when the sum of the edge surface thickness and the threshold value is at least about the same as the main surface thickness. Residue would not be considered present on the edge surface when the sum of the edge surface thickness and the threshold value is up to about the same as the main surface thickness. As would be obvious to those skilled in the art, the calculations for the surface thickness and comparisons can be performed in various configurations. These calculations described are merely illustrative of specific embodiments and other mathematical operations are considered within the scope of the invention.

One or more embodiments of the invention can be used to measure the width of the edge delete zone. This can be accomplished, for example, by measuring the distance from the laser sensor 18 to a plurality of points including the main surface 13, the edge surface 15 and the flat support surface 19. A profile of the distances from the laser sensor 18 along the edge of the substrate 12 can be measured. This profile can include distance measurements taken at the main surface 13, the edge surface 15 and the flat support surface 19. If the distance between the measurement points is known, a first edge of the edge surface 15 would be measured at the point where the main surface 13 transitions to the edge surface 15, and a the second edge of the edge surface 15 would be measured at the point where the edge surface 15 transitions to the flat support surface 19. The width of the edge surface 15 can be measured in conjunction with, or separate from, the determination of whether residue is present on the edge surface 15.

Figure 6A:
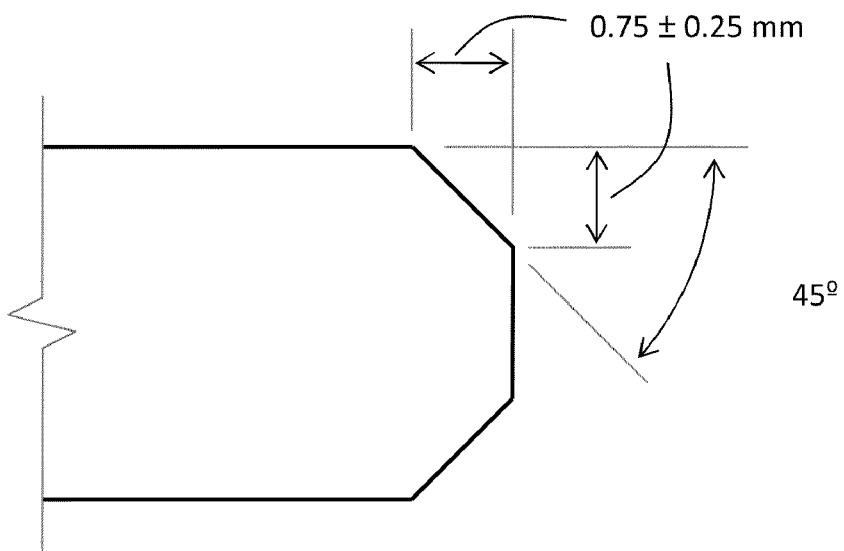
FIGS. 6A and 6B illustrate substrate edge profiles measurable with one or more embodiments of the invention.
Figure 6B:
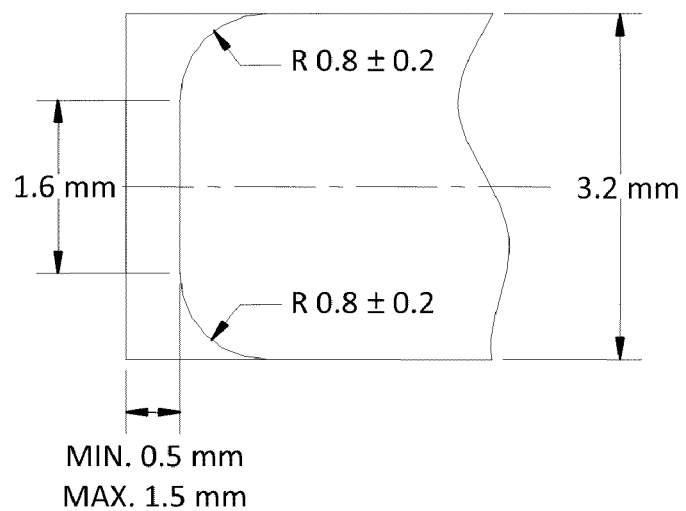

Additionally, one or more embodiments of the invention can be used to measure the quality of the seaming operation, i.e., the measurement of the width and depth of the seamed edge of the glass. FIGS. 6A and 6B show substrate edge profiles having a K-shape and a C-shape, respectively. The relevant measurements of these edges, i.e., radius and edge height, can be determined using embodiments of the invention.

Figure 7:
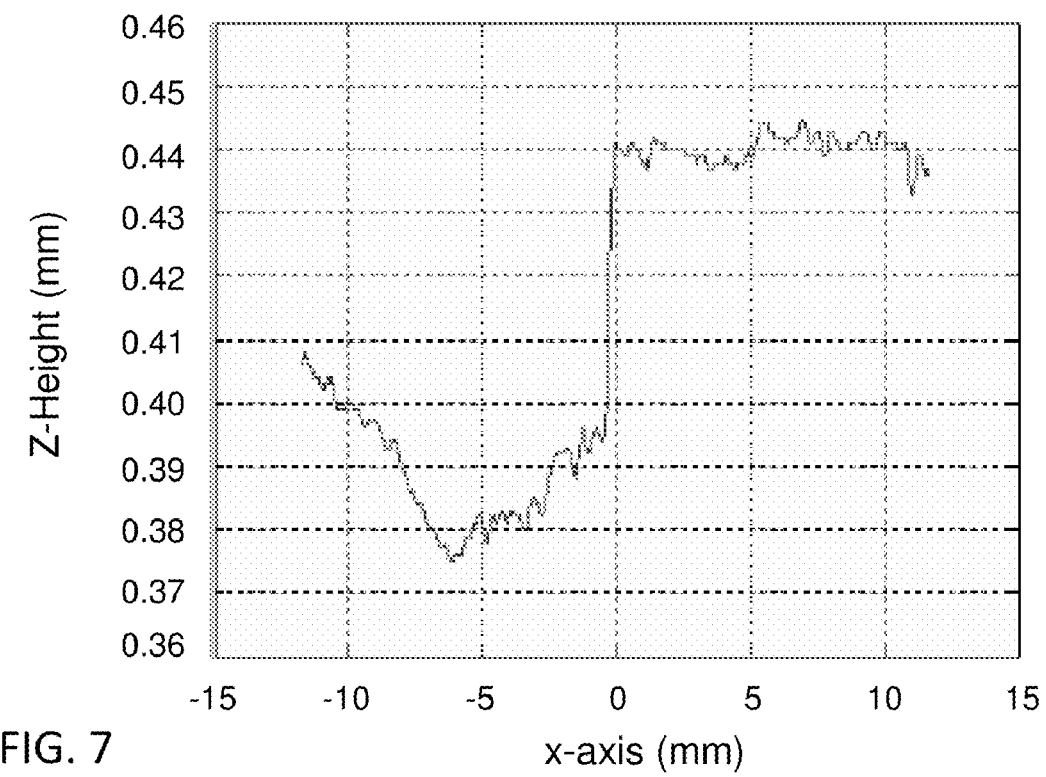
FIG. 7 is a graph showing an edge delete zone without residue using the apparatus of a specific embodiment of the invention.

FIG. 7 shows an example graph of the minimum height of the edge delete surface as a function of the x-axis position along the edge delete zone. It can be seen that each of the data points has a height greater than about 0.03 mm (0.44-0.41 mm based on the minimum values) or 0.05 mm (0.44mm-0.39 mm based on the average values) further from the sensor head than the main surface of the substrate. This graph shows that the edge delete zone is residue free with a height about 0.03 mm (based on minimum) or about 0.01 (based on the average) mm below the thin film surface.

Figure 8:
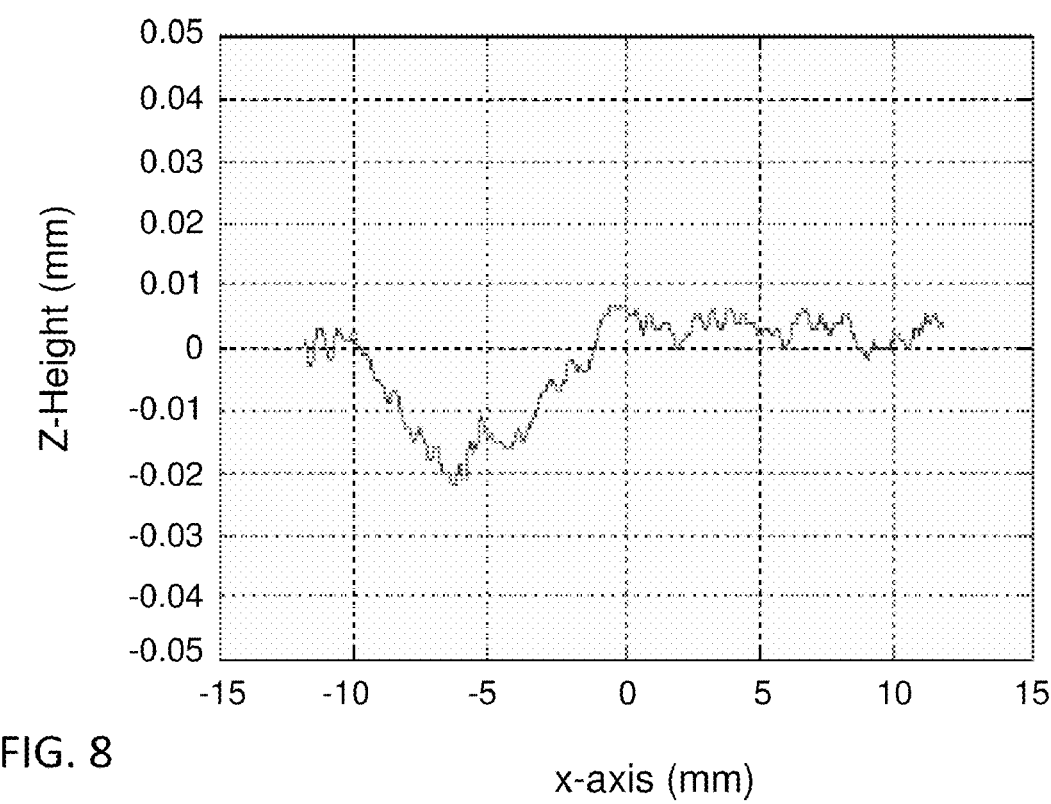
FIG. 8 is a graph showing an edge delete zone with residue using the apparatus of a specific embodiment of the invention.

FIG. 8 shows an example graph of the minimum height of the edge delete surface as a function of the x-axis position along the edge delete zone for another sample. The data is roughly equal to 0 mm (based on the minimum step height because the right and left side are almost the same.), indicating that the edge delete zone height is approximately equal to the height of the main surface. This demonstrates data observed from a sample with residue along the edge delete zone.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments. The order of description of the above method should not be considered limiting, and methods may use the described operations out of order or with omissions or additions.

It is to be understood that the above description is intended to be illustrative, and not restrictive. Many other embodiments will be apparent to those of ordinary skill in the art upon reviewing the above description. The scope of the invention should, therefore, be determined with reference to the appended claims, along with the full scope of equivalents to which such claims are entitled.

The invention claimed is:

1. An apparatus for detecting residue on a portion of a glass substrate surface comprising:
    a platform configured to support the substrate having a ground edge portion, the platform including a table having a pair of parallel side members and a plurality of cross members attached to the side members, each of the cross members having a plurality of supports adapted to support the substrate;
    a laser sensor having at least one sensor head arranged such that the sensor and the substrate can be moved with respect to each other so that the sensor traverses the substrate surface, including a main surface and the ground edge portion of the substrate surface;
    a controller in communication with the sensor head to receive data from the sensor head, the controller operable to interpret data obtained from the sensor head to determine if residue is present on the edge surface.

2. The apparatus of claim 1, wherein the platform further comprises
    a locking frame for preventing the table from moving while in use.

3. The apparatus of claim 2, further comprising a substantially flat surface for holding the substrate, the flat surface positioned on the supports.

4. The apparatus of claim 1, wherein the sensor head has a height difference resolution greater than about 1 μm.

5. The apparatus of claim 1, wherein the laser sensor measures diffuse reflections from the substrate.

6. The apparatus of claim 1, wherein the sensor is operative to measure an average main surface distance from a laser sensor from a plurality of measurements across the main surface and a minimum edge distance, or average edge distance, from the laser sensor; and the controller is operative to determine whether residue is present on the edge surface by comparing the minimum edge distance, or average edge distance, from the laser sensor to the average main surface distance from the laser sensor.

7. The apparatus of claim 1, wherein the sensor and the controller are operative to determine an average thickness of the main surface from a plurality of measurements obtained with a laser sensor spaced from the main surface and to determine a maximum thickness, or average thickness, of the edge portion from a plurality of measurements obtained from the laser sensor; and to determine whether residue is present on the edge surface by comparing the maximum edge thickness, or average edge thickness, to the average main surface thickness.

8. The apparatus of claim 1, further comprising a peripheral device in communication with the controller to receive information from the controller and the laser sensor, the peripheral device capable of graphically displaying information on whether residue exists on the edge portion of the substrate.

9. A method of detecting residue on a glass substrate including a main surface having a height and a coating thereon and an edge surface having a height that is not greater than the height of the main surface, the method comprising:
    positioning a laser sensor a distance from the main surface;
    obtaining an average main surface distance from a laser sensor from a plurality of measurements across the main surface;
    measuring a minimum edge distance or average edge distance from the laser sensor; and
    determining whether residue is present on the edge surface by comparing the minimum edge distance or average edge distance from the laser sensor to the average main surface distance from the laser sensor.

10. The method of claim 9, further comprising establishing a threshold value, the threshold value being a distance value.

11. The method of claim 10, wherein determining whether residue is present on the edge surface comprises:
    concluding that residue is present on the edge surface when the minimum edge distance or average edge distance from the laser sensor is about the same as the sum of the average main surface distance from the laser sensor and the threshold value; and
    concluding that residue is not present on the edge surface when the minimum edge distance or average edge distance from the laser sensor is greater than the sum of the average main surface distance from the laser sensor and the threshold value.

12. The method of claim 9, wherein obtaining an average main surface distance from the laser sensor comprises:
    placing the substrate on a flat surface;
    positioning the laser sensor above the main surface;
    scanning the main surface with the laser sensor and measuring a plurality of distances between the laser sensor and the main surface throughout the scan; and
    calculating an average distance between the main surface and the laser sensor from the plurality of distances.

13. The method of claim 9, wherein measuring a minimum edge distance or average edge distance from the laser sensor comprises:
    placing the substrate on a flat surface;
    positioning the laser sensor above the edge surface;
    scanning the edge surface with the laser sensor and measuring a plurality of distances between the laser sensor and the edge surface throughout the scan; and
    determining the minimum distance or average edge distance between the laser sensor and the edge surface from the plurality of distances.

14. The method of claim 9, wherein the edge has a width in the range of about 10 mm to about 14 mm.

15. A method of detecting residue on a glass substrate including a main surface having a coating thereon defining a main surface thickness and an edge surface having a thickness that is not greater than the thickness of the main surface, the method comprising:

determining an average thickness of the main surface from a plurality of measurements obtained with a laser sensor spaced from the main surface;

determining a maximum thickness or average thickness of the edge surface from a plurality of measurements using the laser sensor; and determining whether residue is present on the edge surface by comparing the maximum edge thickness or average edge thickness to the average main surface thickness.

16. The method of claim 15, wherein determining the average thickness of the main surface comprises:

measuring an average reference distance between the laser sensor and a flat support surface using a plurality of measurements;

placing the substrate on the flat support surface;

measuring an average main surface distance between the laser sensor and the main surface of the substrate using a plurality of measurements; and determining the thickness of the substrate main surface by subtracting the average main surface distance from average reference distance.

17. The method of claim 15, wherein determining the maximum thickness or average thickness of the edge surface comprises:

measuring an average reference distance between the laser sensor and a flat support surface using a plurality of measurements;

placing the substrate on the flat support surface;

measuring an minimum edge surface distance or average edge surface between the laser sensor and the edge surface of the substrate using a plurality of measurements; and determining the thickness of the edge surface by subtracting the minimum edge surface distance or average edge surface distance from average reference distance.

18. The method of claim 15, further comprising establishing a threshold value representing a thickness.

19. The method of claim 18, wherein determining whether residue is present on the edge surface comprising:

concluding that residue is present on the edge surface when the sum of the edge surface thickness and the threshold value is at least about the same as the main surface thickness; and concluding that residue is not present on the edge surface when the sum of the edge surface thickness and the threshold value is less than the main surface thickness.

20. The method of claim 15, wherein the edge has a width in the range of about 10 mm to about 14 mm.

\* \* \* \* \*